US012731675B2

(12) United States Patent
Masumoto et al.

(10) Patent No.: US 12,731,675 B2
(45) Date of Patent: Sep. 8, 2026

(54) MEDICAL IMAGE DIAGNOSTIC SYSTEM FOR DERIVING DEGREE OF CONTRIBUTION IN MEDICAL IMAGE DIAGNOSIS, MEDICAL IMAGE DIAGNOSTIC SYSTEM EVALUATION METHOD, AND PROGRAM

(71) Applicant: FUJIFILM Corporation, Tokyo (JP)

(72) Inventors: Jun Masumoto, Tokyo (JP); Masaharu Morita, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 364 days.

(21) Appl. No.: 18/533,050

(22) Filed: Dec. 7, 2023

(65) Prior Publication Data

US 2024/0105315 A1 Mar. 28, 2024

Related U.S. Application Data

(63) Continuation of application No. PCT/JP2022/014071, filed on Mar. 24, 2022.

(30) Foreign Application Priority Data

Jun. 17, 2021 (JP) ................................ 2021-100612

(51) Int. Cl.

*G06T 7/00* (2017.01)
*G16H 30/40* (2018.01)
*G16H 50/20* (2018.01)

(52) U.S. Cl.

CPC ........... *G16H 30/40* (2018.01); *G06T 7/0012* (2013.01); *G16H 50/20* (2018.01);
(Continued)

(58) Field of Classification Search

CPC ........ G16H 30/40; G16H 50/20; G16H 30/20; G06T 7/0012; G06T 2207/20081;
(Continued)

(56) References Cited

U.S. PATENT DOCUMENTS 10,269,114 B2 4/2019 Reicher et al.
2004/0100476 A1* 5/2004 Morita .................... H04N 7/18 345/619

(Continued)

FOREIGN PATENT DOCUMENTS

JP 2006043007 2/2006
JP 2006167289 6/2006

(Continued)

OTHER PUBLICATIONS

"Search Report of Europe Counterpart Application", issued on Jul. 11, 2024, pp. 1-10.

(Continued)

*Primary Examiner* — Siamak Harandi
(74) *Attorney, Agent, or Firm* — JCIPRNET

(57) ABSTRACT

A first discrimination result (24A) is acquired from a first discrimination device (16A), a second discrimination result (24B) is acquired from a second discrimination device (16B) that executes second discrimination intended for the same site and the same lesion as those for which discrimination of the first discrimination device is intended, an integrated discrimination result (26) in which the first discrimination result and the second discrimination result are integrated is derived, and a degree of contribution of the first discrimination device to the integrated discrimination result and a degree of contribution of the second discrimination device to the integrated discrimination result are derived based on the integrated discrimination result and a definitive diagnosis result by a doctor.

10 Claims, 8 Drawing Sheets

(52) U.S. Cl.
CPC ............... *G06T 2207/20081* (2013.01); *G06T 2207/20084* (2013.01); *G06T 2207/30096* (2013.01)

(58) Field of Classification Search
CPC . G06T 2207/20084; G06T 2207/30096; G06T 2207/10072; G06T 2207/10116; G06T 2207/30048; G06T 2207/30061; A61B 6/03
See application file for complete search history.

(56) References Cited

U.S. PATENT DOCUMENTS

| | | | | |
|---|---|---|---|---|
| 2014/0101080 | A1 | 4/2014 | Lee et al. | |
| 2020/0104996 | A1* | 4/2020 | Akahori | G16H 50/20 |
| 2020/0202523 | A1 | 6/2020 | Ahn | |
| 2021/0125724 | A1 | 4/2021 | Kawahara et al. | |
| 2021/0193299 | A1* | 6/2021 | Satoh | G16H 30/40 |

FOREIGN PATENT DOCUMENTS

| | | |
|---|---|---|
| JP | 4480508 | 6/2010 |
| JP | 2013005841 | 1/2013 |
| KR | 101818074 | 1/2018 |

OTHER PUBLICATIONS

"International Search Report (Form PCT/ISA/210) of PCT/JP2022/014071," mailed on May 10, 2022, with English translation thereof, pp. 1-5.

"Written Opinion of the International Searching Authority (Form PCT/ISA/237) of PCT/ JP2022/014071," mailed on May 10, 2022, with English translation thereof, pp. 1-8.

"Office Action of Japan Counterpart Application", issued on Jul. 9, 2025, with English translation thereof, pp. 1-6.

* cited by examiner

FIG. 4

| TIMES | CAD PROCESSING SERVER 16A MANUFACTURED BY COMPANY A | | CAD PROCESSING SERVER 16B MANUFACTURED BY COMPANY B | | CAD PROCESSING SERVER 16C MANUFACTURED BY COMPANY C | |
|---|---|---|---|---|---|---|
| 1 | DETECTION | ADOPTION | NON-DETECTION | - | DETECTION | NON-ADOPTION |
| 2 | DETECTION | ADOPTION | DETECTION | NON-ADOPTION | DETECTION | ADOPTION |
| 3 | DETECTION | ADOPTION | NON-DETECTION | - | DETECTION | ADOPTION |
| 4 | DETECTION | ADOPTION | NON-DETECTION | - | DETECTION | ADOPTION |
| ⋮ | ⋮ | ⋮ | ⋮ | ⋮ | ⋮ | ⋮ |
| N | ⋮ | ⋮ | ⋮ | ⋮ | ⋮ | ⋮ |

FIG. 5

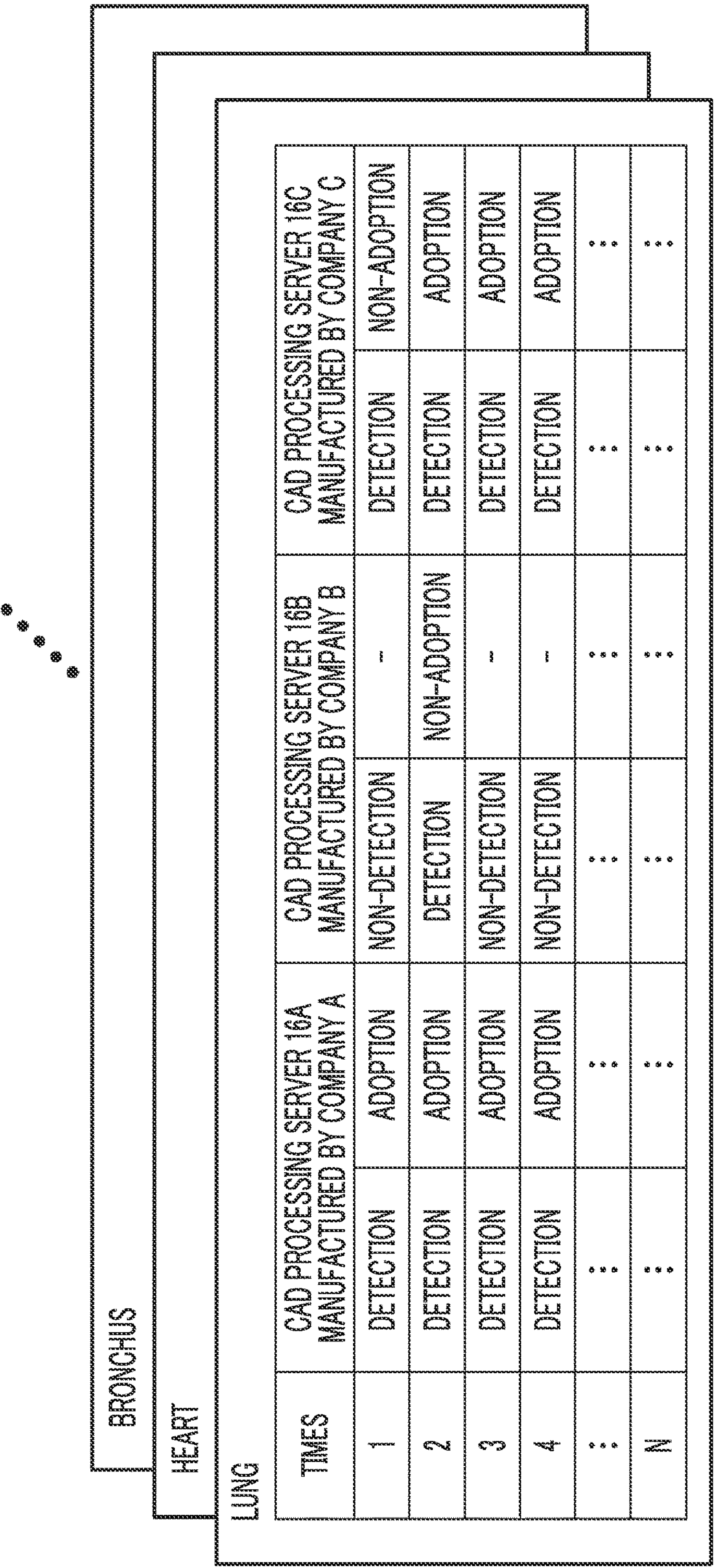

| TIMES | CAD PROCESSING SERVER 16A MANUFACTURED BY COMPANY A | | CAD PROCESSING SERVER 16B MANUFACTURED BY COMPANY B | | CAD PROCESSING SERVER 16C MANUFACTURED BY COMPANY C | |
|---|---|---|---|---|---|---|
| 1 | DETECTION | ADOPTION | NON-DETECTION | – | DETECTION | NON-ADOPTION |
| 2 | DETECTION | ADOPTION | DETECTION | NON-ADOPTION | DETECTION | ADOPTION |
| 3 | DETECTION | ADOPTION | NON-DETECTION | – | DETECTION | ADOPTION |
| 4 | DETECTION | ADOPTION | NON-DETECTION | – | DETECTION | ADOPTION |
| ⋮ | ⋮ | ⋮ | ⋮ | ⋮ | ⋮ | ⋮ |
| N | ⋮ | ⋮ | ⋮ | ⋮ | ⋮ | ⋮ |

FIG. 6

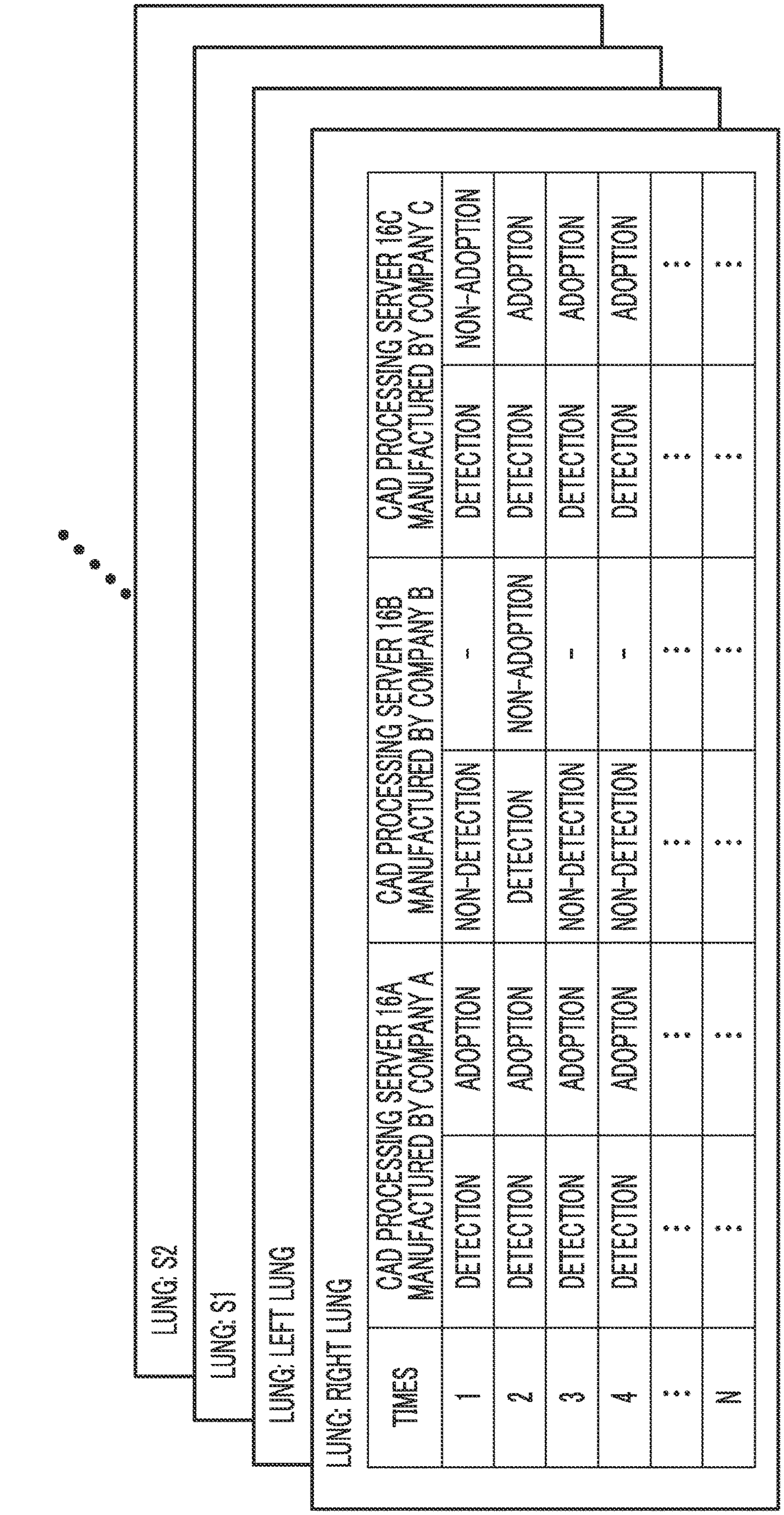

| TIMES | CAD PROCESSING SERVER 16A MANUFACTURED BY COMPANY A | | CAD PROCESSING SERVER 16B MANUFACTURED BY COMPANY B | | CAD PROCESSING SERVER 16C MANUFACTURED BY COMPANY C | |
|---|---|---|---|---|---|---|
| 1 | DETECTION | ADOPTION | NON-DETECTION | – | DETECTION | NON-ADOPTION |
| 2 | DETECTION | ADOPTION | DETECTION | NON-ADOPTION | DETECTION | ADOPTION |
| 3 | DETECTION | ADOPTION | NON-DETECTION | – | DETECTION | ADOPTION |
| 4 | DETECTION | ADOPTION | NON-DETECTION | – | DETECTION | ADOPTION |
| ⋮ | ⋮ | ⋮ | ⋮ | ⋮ | ⋮ | ⋮ |
| N | ⋮ | ⋮ | ⋮ | ⋮ | ⋮ | ⋮ |

120
$I_1$
$T_2$
2011092107
CT02/03/2010
000,001,Monitor,CT
C Over P1
NO ABNORMALITY IS FOUND USING CAD MANUFACTURED BY COMPANY B.
104
102

MEDICAL IMAGE DIAGNOSTIC SYSTEM FOR DERIVING DEGREE OF CONTRIBUTION IN MEDICAL IMAGE DIAGNOSIS, MEDICAL IMAGE DIAGNOSTIC SYSTEM EVALUATION METHOD, AND PROGRAM

CROSS-REFERENCE TO RELATED APPLICATIONS

The present application is a Continuation of PCT International Application No. PCT/JP2022/014071 filed on Mar. 24, 2022 claiming priority under 35 U.S.C § 119(a) to Japanese Patent Application No. 2021-100612 filed on Jun. 17, 2021. Each of the above applications is hereby expressly incorporated by reference, in its entirety, into the present application.

BACKGROUND OF THE INVENTION

1. Field of the Invention

The present invention relates to a medical image diagnostic system, a medical image diagnostic system evaluation method, and a program.

2. Description of the Related Art

There is known a medical image diagnosis support system that uses applied artificial intelligence (AI) to discover and diagnose an abnormal region in a medical image. The medical image diagnosis support system is called a CAD which is an abbreviation for Computer Aided Diagnosis in English. An era is envisioned in which a plurality of CADs can be used for the same site and the same lesion.

For example, in an image diagnostic platform where a plurality of CADs provided by a plurality of companies are adopted, discrimination processing using each of the plurality of CADs is executed on one medical image to be processed. A user such as a doctor can refer to a discrimination result of each of the plurality of CADs.

JP2006-167289A discloses a composite image diagnosis support system that acquires a diagnosis result output from each of a plurality of computer-aided diagnostic apparatuses, applies a prescribed determination criterion to determine a final result as a system, and presents the final result to an operator such as a doctor. In JP2006-167289A, a computer-aided diagnostic apparatus is called a Computer Aided Diagnosis (CAD).

SUMMARY OF THE INVENTION

However, even in a case in which the medical image is intended for the same site and the same lesion, the discrimination and diagnosis of the medical image in which a plurality of different CAD processing results are integrated are cumbersome for a doctor.

The system disclosed in JP2006-167289A aims to automatically construct a new database by distributing images from which the final results are derived to a diseased image database and a disease-free image database. The system disclosed in JP2006-167289A does not focus on the above problem, and JP2006-167289A does not disclose components that solve the above problem.

The present invention has been made in view of such circumstances, and an object of the present invention is to provide a medical image diagnostic system, a medical image diagnostic system evaluation method, and a program capable of grasping contribution of each of a plurality of discrimination results with respect to an integrated discrimination result in which the plurality of discrimination results are integrated.

According to the present disclosure, there is provided a medical image diagnostic system comprising: a processor; and a memory that stores one or more commands executed by the processor, in which the processor acquires a first discrimination result from a first discrimination device that executes first discrimination intended for a predetermined site and a predetermined lesion, on a medical image, acquires a second discrimination result from a second discrimination device that executes second discrimination intended for the predetermined site and the predetermined lesion, which are the same as those for which the discrimination of the first discrimination device is intended, on the medical image, derives an integrated discrimination result in which the first discrimination result and the second discrimination result are integrated, and derives a degree of contribution of the first discrimination device to the integrated discrimination result and a degree of contribution of the second discrimination device to the integrated discrimination result based on the integrated discrimination result and a definitive diagnosis result by a doctor.

With the medical image diagnostic system according to the present disclosure, the degree of contribution of the first discrimination result to the integrated discrimination result and the degree of contribution of the second discrimination result to the integrated discrimination result are derived based on the integrated discrimination result. Accordingly, it is possible to grasp the contribution of the first discrimination device and the second discrimination device in the integrated discrimination result in which a plurality of discrimination results are integrated.

In the medical image diagnostic system according to another aspect, the processor derives the integrated discrimination result by using an integrated discrimination device, which is a trained learning model that has trained using a set of the medical image and a correct answer image in which a lesion is detected from the medical image, as learning data.

According to such an aspect, it is possible to improve a discrimination accuracy in the integrated discrimination result.

As the correct answer image, a lesion mask image in which a lesion is shown in the medical image can be used.

In the medical image diagnostic system according to still another aspect, the integrated discrimination device uses the trained learning model that has trained using a set of first correct answer data output from the first discrimination device in a case in which the medical image is input to the first discrimination device, second correct answer data output from the second discrimination device in a case in which the medical image is input to the second discrimination device, and the correct answer image, as learning data.

According to such an aspect, it is possible to improve a discrimination accuracy in the integrated discrimination result.

In the medical image diagnostic system according to still another aspect, the processor derives a first score representing the degree of contribution of the first discrimination device to the integrated discrimination result, and derives a second score representing the degree of contribution of the second discrimination device to the integrated discrimination result.

According to such an aspect, it is possible to evaluate the contribution of the first discrimination device and the second discrimination device to the integrated discrimination result based on the numerical degree of contribution as the score.

In the medical image diagnostic system according to still another aspect, the processor evaluates the contribution of the first discrimination device and the second discrimination device to the integrated discrimination result, for each predetermined site.

According to such an aspect, it is possible to evaluate the characteristics of the first discrimination device and the characteristics of the second discrimination device for each site.

In the medical image diagnostic system according to still another aspect, the processor evaluates the contribution of the first discrimination device and the second discrimination device to the integrated discrimination result, for each region obtained by subdividing the predetermined site.

According to such an aspect, it is possible to execute contribution evaluation with respect to the integrated discrimination result in which the characteristics of each region obtained by subdividing sites in a first discrimination model and a second discrimination model are reflected.

In the medical image diagnostic system according to still another aspect, the processor causes a display device to display at least one of the first discrimination result or the second discrimination result.

According to such an aspect, it is possible for a user such as the doctor to grasp at least one of the first discrimination result or the second discrimination result.

In the medical image diagnostic system according to still another aspect, the processor acquires input information representing the definitive diagnosis result by the doctor, which is input by using an input device.

According to such an aspect, it is possible for the user such as the doctor to input the definitive diagnosis result by the doctor by using the input device.

The medical image diagnostic system according to still another aspect further comprises: an image storage device that stores the medical image, in which the processor acquires the medical image from the image storage device.

According to such an aspect, it is possible to acquire the medical image from the image storage device.

In the medical image diagnostic system according to still another aspect, the medical image diagnostic system includes the first discrimination device and the second discrimination device.

According to such an aspect, it is possible to configure a medical image diagnostic system provided with the first discrimination device and the second discrimination device.

According to the present disclosure, there is provided a medical image diagnostic system evaluation method executed by a computer, the method comprising: acquiring a first discrimination result obtained by executing first discrimination intended for a predetermined site and a predetermined lesion, on a medical image; acquiring a second discrimination result obtained by executing second discrimination intended for the predetermined site and the predetermined lesion, which are the same as those for which the first discrimination is intended, on the medical image; deriving an integrated discrimination result in which the first discrimination result and the second discrimination result are integrated; and deriving a degree of contribution of the first discrimination to the integrated discrimination result and a degree of contribution of the second discrimination to the integrated discrimination result based on the integrated discrimination result and a definitive diagnosis result by a doctor.

With the medical image diagnostic system evaluation method according to the present disclosure, it is possible to obtain the same effects as those of the medical image diagnostic system according to the present disclosure. Configuration requirements of the medical image diagnostic system according to another aspect can be applied to configuration requirements of the medical image diagnostic system evaluation method according to another aspect.

According to the present disclosure, there is provided a program for causing a computer to execute: acquiring a first discrimination result obtained by executing first discrimination intended for a predetermined site and a predetermined lesion, on a medical image; acquiring a second discrimination result obtained by executing second discrimination intended for the predetermined site and the predetermined lesion, which are the same as those for which the first discrimination is intended, on the medical image; deriving an integrated discrimination result in which the first discrimination result and the second discrimination result are integrated; and deriving a degree of contribution of the first discrimination to the integrated discrimination result and a degree of contribution of the second discrimination to the integrated discrimination result based on the integrated discrimination result and a definitive diagnosis result by a doctor.

With the program according to the present disclosure, it is possible to obtain the same effects as those of the medical image diagnostic system according to the present disclosure. Configuration requirements of the medical image diagnostic system according to another aspect can be applied to configuration requirements of the program according to another aspect.

According to the present invention, the degree of contribution of the first discrimination result to the integrated discrimination result and the degree of contribution of the second discrimination result to the integrated discrimination result are derived based on the integrated discrimination result. Accordingly, it is possible to grasp the contribution of the first discrimination device and the second discrimination device in the integrated discrimination result in which a plurality of discrimination results are integrated.

BRIEF DESCRIPTION OF THE DRAWINGS

FIG. 4 is a table showing an example of an evaluation result of a CAD processing server.

FIG. 5 is a schematic diagram showing a configuration example of an evaluation result of the CAD processing server.

FIG. 6 is a schematic diagram showing another configuration example of an evaluation result of the CAD processing server.

DESCRIPTION OF THE PREFERRED EMBODIMENTS

Figure 1:
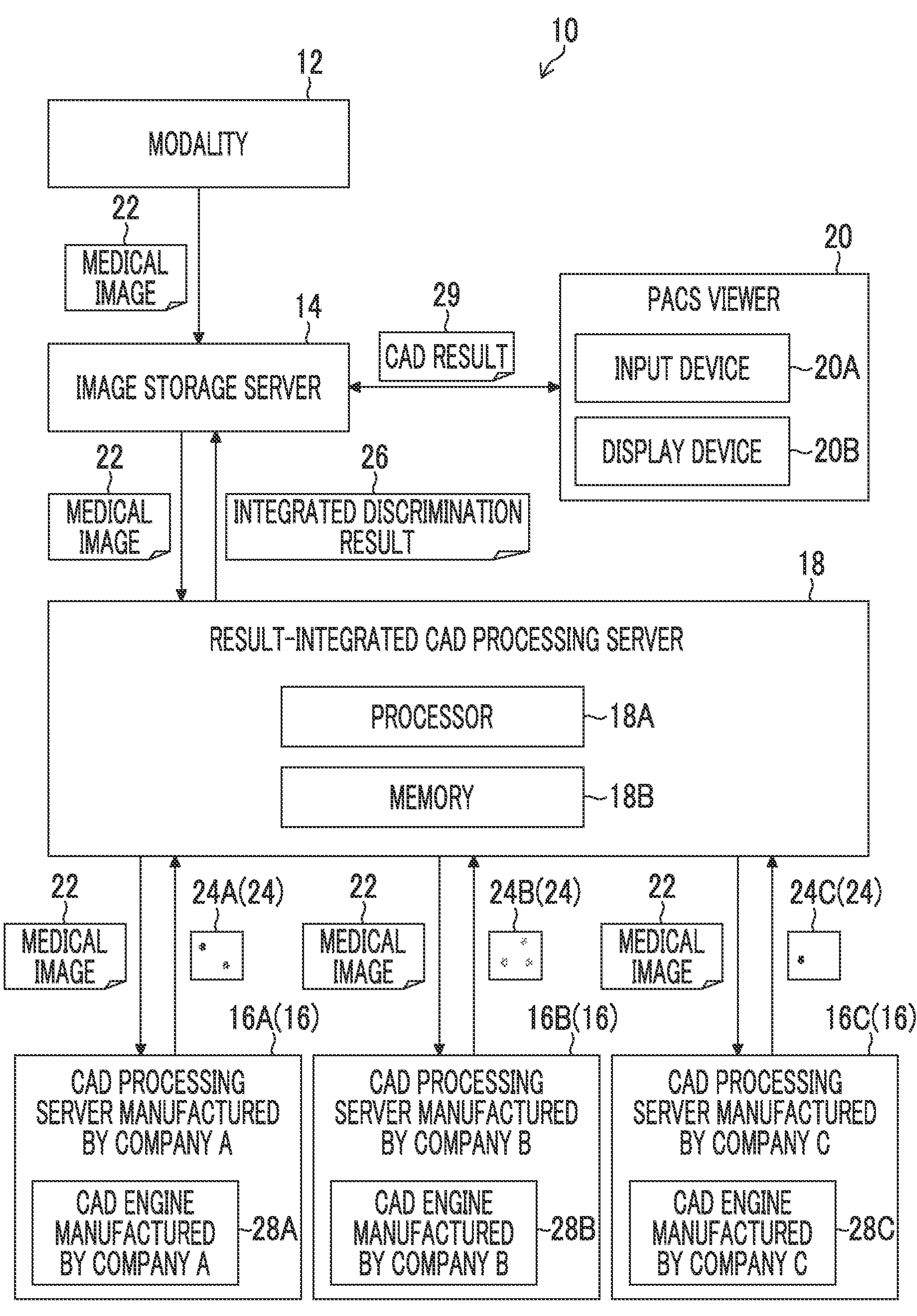
FIG. 1 is a block diagram of a medical image diagnostic system according to an embodiment.

Hereinafter, a preferred embodiment of the present invention will be described with reference to the accompanying drawings. In the present specification, the same components are denoted by the same reference numerals, and duplicate description thereof will be omitted as appropriate.

[Configuration Example of Medical Image Diagnostic System]

FIG. 1 is a block diagram of a medical image diagnostic system according to an embodiment. A medical image diagnostic system 10 shown in FIG. 1 comprises a modality 12, an image storage server 14, a plurality of CAD processing servers 16, a result-integrated CAD processing server 18, and a PACS viewer 20. The "CAD" is an abbreviation for Computer-Aided Diagnosis. In addition, the "PACS" is an abbreviation for Picture Archiving and Communication System.

In the medical image diagnostic system 10, the modality 12, the image storage server 14, the plurality of CAD processing servers 16, the result-integrated CAD processing server 18, and the PACS viewer 20 can transmit and receive data to and from each other via a communication network such as the Internet.

In the present embodiment, an aggregate of a plurality of devices is called a system, but the term "system" can include the concept of a device. That is, the terms "system" and "device" can be replaced with each other.

The modality 12 is an imaging apparatus that captures an image of an examination target site of a subject and generates a medical image 22. Examples of the modality 12 include an X-ray imaging apparatus, a CT apparatus, an MRI apparatus, a PET apparatus, an ultrasound apparatus, and a CR apparatus using a flat X-ray detector. Here, the term "medical image" is synonymous with a medical-use image.

The "CT" is an abbreviation for Computed Tomography. The "MM" is an abbreviation for Magnetic Resonance Imaging. The "PET" is an abbreviation for Positron Emission Tomography. The "CR" is an abbreviation for Computed Radiography.

The image storage server 14 is a server that manages the medical image 22 captured by using the modality 12. As the image storage server 14, a computer comprising a large-capacity storage device is used. A program that provides a function of a data storage system is incorporated in the computer. The image storage server 14 acquires the medical image 22 captured by the modality 12, and stores the medical image 22 in a large-capacity storage device. The program is synonymous with software. The image storage server 14 described in the embodiment is an example of an image storage device that stores the medical image.

A DICOM standard can be applied as a format of the medical image 22. DICOM tag information defined by the DICOM standard may be added to the medical image 22. The term "image" can include the meaning of image data which is a signal indicating an image, as well as the meaning of an image itself such as a photograph. The "DICOM" is an abbreviation for Digital Imaging and Communications in Medicine.

FIG. 1 illustrates, as the plurality of CAD processing servers 16, a CAD processing server 16A manufactured by Company A, a CAD processing server 16B manufactured by Company B, and a CAD processing server 16C manufactured by Company C, which are manufactured by three different companies. The CAD processing servers 16 need only be provided in plural, the number is not limited.

The plurality of CAD processing servers 16 execute abnormality detection processing for each site, on the medical image 22 acquired from the image storage server 14 and discriminate the presence or absence of an abnormality in the medical image. Each of the plurality of CAD processing servers 16 can execute abnormality detection processing for a predetermined site and a predetermined lesion by using the same medical image 22. That is, each of the plurality of CAD processing servers 16 can execute the abnormality detection processing for the same site and the same lesion based on the same medical image 22. Examples of the site include an organ, a bone, a muscle, a ligament, a nerve, and a blood vessel. Examples of the abnormality include a disorder, a disease, and a lesion. A discrimination result 24 in each of the plurality of CAD processing servers 16 is associated with the medical image 22 to be processed and transmitted to the result-integrated CAD processing server 18.

The term "detection" can include the concept of "extraction". In addition, the term "discrimination" can include the concepts such as identification, recognition, inference, estimation, and detection.

FIG. 1 shows an example in which a discrimination result 24A is output from the CAD processing server 16A manufactured by Company A, a discrimination result 24B is output from the CAD processing server 16B manufactured by Company B, and a discrimination result 24C is output from the CAD processing server 16C manufactured by Company C.

As the discrimination result 24 output from the CAD processing server 16, a binary image in which a pixel value of a pixel detected as an abnormality is set to 1 and a pixel value of a pixel not detected as an abnormality is set to 0 can be used. FIG. 1 illustrates the discrimination result 24A, the discrimination result 24B, and the discrimination result 24C in which a binary image is used.

Each of the plurality of CAD processing servers 16 shown in FIG. 1 comprises one or more processors and one or more memories. In the CAD processing server 16, the processor executes a command included in a program stored in the memory to discriminate the medical image 22 and to output the discrimination result 24.

The CAD processing server 16A manufactured by Company A is equipped with a CAD engine 28A manufactured by Company A. The CAD engine 28A manufactured by Company A executes the abnormality detection processing of the medical image 22 in the CAD processing server 16A manufactured by Company A, and outputs the discrimination result 24A.

The CAD processing server 16B manufactured by Company B is equipped with a CAD engine 28B manufactured by Company B. The CAD engine 28B manufactured by Company B executes the abnormality detection processing of the medical image 22 in the CAD processing server 16B manufactured by Company B, and outputs the discrimination result 24B.

The CAD processing server 16C manufactured by Company C is equipped with a CAD engine 28C manufactured by Company C. The CAD engine 28C manufactured by Company C executes the abnormality detection processing of the medical image 22 in the CAD processing server 16C manufactured by Company C, and outputs the discrimination result 24C. The CAD engine 28A manufactured by Company A, the CAD engine 28B manufactured by Company B, and the CAD engine 28C manufactured by Company C can use a trained learning model such as a convolutional neural network called a CNN.

The result-integrated CAD processing server 18 acquires each discrimination result 24 for one medical image 22 transmitted from each of the plurality of CAD processing servers 16, and generates an integrated discrimination result 26 based on each discrimination result 24 for one medical image 22. The integrated discrimination result 26 is associated with the medical image 22 to be processed, is transmitted to the image storage server 14, and is stored in the image storage server 14.

A trained learning model is used for the result-integrated CAD processing server 18. A convolutional neural network is used as an example of the learning model applied to the result-integrated CAD processing server 18.

The convolutional neural network can adopt a configuration including a combination of a convolutional layer and a pooling layer in a part of a plurality of interlayers. The number of the plurality of interlayers constituting the convolutional neural network, the content of processing of each layer, and the arrangement order of each layer are not limited, and a structure formed of various combinations can be adopted.

The convolutional layer acquires a feature map by performing convolution calculation using a filter to a node present in a local region in the front layer. The convolutional layer is responsible for feature extraction of extracting a featured intensity structure represented by the filter from the image.

The pooling layer performs pooling processing of aggregating the local regions of the feature map output from the convolutional layer into a representative value. The pooling layer generates a new feature map of which a resolution is decreased by reducing the feature map output from the convolutional layer.

The pooling layer provides robustness such that the target feature amount extracted using the convolutional layer is not affected by the positional fluctuation. In other words, the pooling layer reduces the sensitivity of the target feature amount to the positional fluctuation.

The convolutional neural network may include one or more of at least one type of layer of a normalization layer or a fully-connected layer, in addition to the convolutional layer and the pooling layer. In addition, each layer of the interlayers may include an activation function as necessary.

The normalization layer performs processing of normalizing the intensity structure of the image. For example, the normalization layer performs local contrast normalization on at least one output of the output of the convolutional layer or the output of the pooling layer.

The fully-connected layer is a layer in which all nodes between adjacent layers are connected. The fully-connected layer may be disposed near the output layer. For example, the fully-connected layer connects the feature map from which a feature is extracted through the convolutional layer and the pooling layer to one node, and outputs a feature variable using the activation function. In general, in the convolutional neural network, one or more fully-connected layers are disposed between the last pooling layer and the output layer. The output layer performs class classification using a softmax function or the like based on the output from the fully-connected layer.

The result-integrated CAD processing server 18 evaluates CAD processing performance such as the characteristics and features of the CAD processing for each of the plurality of CAD processing servers 16 based on the integrated discrimination result 26. The result-integrated CAD processing server 18 stores a result of the CAD processing performance evaluation of each of the plurality of CAD processing servers 16.

In addition, the result-integrated CAD processing server 18 acquires definitive diagnosis information representing a definitive diagnosis result by a doctor, and evaluates contribution of the CAD processing to the integrated discrimination result 26 based on the integrated discrimination result 26 and the definitive diagnosis result by the doctor. The definitive diagnosis information described in the embodiment is an example of input information representing the definitive diagnosis result by the doctor.

The result-integrated CAD processing server 18 stores a result of the contribution evaluation of the CAD processing of each of the plurality of CAD processing servers 16 to the integrated discrimination result 26. Details of the performance evaluation and the contribution evaluation for the plurality of CAD processing servers 16 will be described below.

As the result-integrated CAD processing server 18, a computer is used. A form of the computer may be a personal computer, or may be a workstation. The result-integrated CAD processing server 18 comprises one or more processors 18A and one or more memories 18B. The processor 18A executes a command stored in the memory 18B.

Here, examples of a hardware structure of the processor 18A include a central processing unit (CPU), a graphics processing unit (GPU), a programmable logic device (PLD), and an application specific integrated circuit (ASIC). The CPU is a general-purpose processor that executes a program to act as various functional units. The GPU is a processor specialized in image processing.

The PLD is a processor capable of changing a configuration of an electric circuit after manufacturing a device. Examples of the PLD include a field programmable gate array (FPGA). The ASIC is a processor comprising a dedicated electric circuit specifically designed to execute specific processing.

One processing unit may be configured of one of these various processors or may be configured of two or more processors of the same type or different types. Examples of a combination of various processors include a combination of one or more FPGAs and one or more CPUs, and a combination of one or more FPGAs and one or more GPUs. Another example of a combination of various processors includes a combination of one or more CPUs and one or more GPUs.

A plurality of functional units may be configured by using one processor. As an example of configuring a plurality of functional units by using one processor, there is an aspect in which, as typified by a computer such as a client or a server, a combination of one or more CPUs and software such as a system on a chip (SoC) is applied to configured one processor, and the processor is caused to act as a plurality of functional units.

As another example of configuring a plurality of functional units by using one processor, there is an aspect in which a processor that realizes functions of an entire system including a plurality of functional units by using one IC chip is used. The "IC" is an abbreviation for Integrated Circuit.

As described above, the various functional units are configured by using one or more of the above described various processors as a hardware structure. Furthermore, the hardware structure of the above described various processors is, more specifically, an electric circuit (circuitry) in which circuit elements such as semiconductor elements are combined.

The memory 18B stores a command executed by the processor 18A. The memory 18B may include a random access memory (RAM) or may include a read only memory (ROM).

The processor 18A uses the RAM as a work region to execute software using various programs and parameters including a medical image processing program stored in the ROM, and executes various types of processing of the result-integrated CAD processing server 18 using the parameters stored in the ROM or the like.

The result-integrated CAD processing server 18 may have the functions of the plurality of CAD processing servers 16. The program used in the plurality of CAD processing servers 16 may be executed using the hardware of the processor 18A of the result-integrated CAD processing server 18. The hardware and software of the plurality of CAD processing servers 16 may be incorporated in the result-integrated CAD processing server 18.

The PACS viewer 20 is a terminal device used by a user such as the doctor. As the PACS viewer 20, a known image viewer for image interpretation is used. The PACS viewer 20 may be a personal computer, a workstation, or a tablet terminal.

The PACS viewer 20 comprises an input device 20A and a display device 20B. Examples of the input device 20A include a pointing device such as a mouse, and an input device such as a keyboard. The user can input an instruction to the medical image diagnostic system 10 by using the input device 20A.

The display device 20B functions as a graphical user interface (GUI) that displays a screen necessary for an operation using the input device 20A. In addition, the display device 20B displays the medical image captured by the modality 12. Further, the integrated discrimination result 26 is displayed as a CAD result 29 on the display device 20B.

That is, the display device 20B receives a display signal representing the CAD result 29 and displays the CAD result 29. The CAD result 29 includes the integrated discrimination result 26. The CAD result 29 may include the discrimination result 24 for each CAD processing server 16.

As the PACS viewer 20, a touch panel display in which the input device 20A and the display device 20B are integrated may be used.

The CAD processing server 16A manufactured by Company A, the CAD processing server 16B manufactured by Company B, and the CAD processing server 16C manufactured by Company C, which are described in the embodiment, are examples of a first discrimination device that executes first discrimination, and are examples of a second discrimination device that executes second discrimination. In other words, each of the CAD processing server 16A manufactured by Company A, the CAD processing server 16B manufactured by Company B, and the CAD processing server 16C manufactured by Company C is any one of the first discrimination device or the second discrimination device. For example, in a case in which the CAD processing server 16A manufactured by Company A is the first discrimination device, the CAD processing server 16B manufactured by Company B and the CAD processing server 16C manufactured by Company C are the second discrimination devices. The discrimination result 24A, the discrimination result 24B, and the discrimination result 24C, which are described in the embodiment, are examples of a first discrimination result, and are examples of a second discrimination result. In other words, each of the discrimination result 24A, the discrimination result 24B, and the discrimination result 24C is any one of the first discrimination result or the second discrimination result. For example, in a case in which the discrimination result 24A is the first discrimination result, the discrimination result 24B and the discrimination result 24C are the second discrimination results. The result-integrated CAD processing server 18 described in the embodiment is an example of an integrated discrimination device.

[Learning Applied to Result-Integrated CAD Processing Server]

Figure 2:
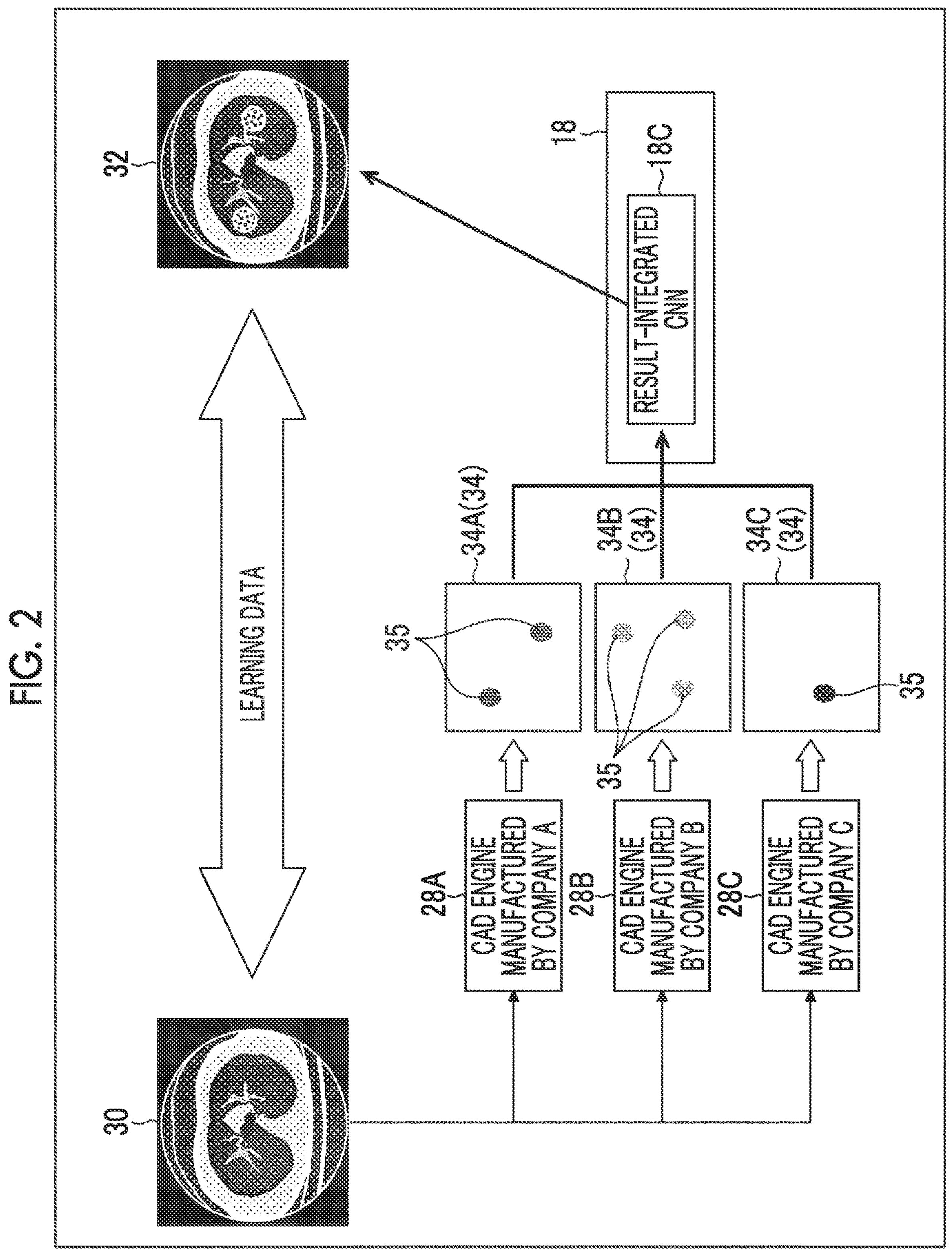
FIG. 2 is a schematic diagram of learning applied to a result-integrated CAD processing server.

FIG. 2 is a schematic diagram of learning applied to the result-integrated CAD processing server. In the learning of the result-integrated CAD processing server 18, a set of a medical image for learning 30 and a correct answer mask image 32 is used as learning data.

As the medical image for learning 30 used as the learning data of the result-integrated CAD processing server 18, a medical image that is captured using the same modality as the medical image used as learning data of the plurality of CAD processing servers 16 is used.

In addition, as the medical image for learning 30, a medical image of the same site and the same lesion as the medical image used as the learning data of the plurality of CAD processing servers 16 is used. On the other hand, as the medical image for learning 30, a medical image that is not used in the learning data of the plurality of CAD processing servers 16 is used.

In FIG. 2, a CT image of a lung is illustrated as the medical image for learning 30, and a lung tumor region mask image is illustrated as the correct answer mask image 32. The lung tumor region mask image can be generated by executing mask processing on a lung tumor region extracted from the CT image of the lung.

The following procedure is used in the learning of the result-integrated CAD processing server 18. The medical image for learning 30 serving as the learning data is input to each of the CAD engine 28A manufactured by Company A, the CAD engine 28B manufactured by Company B, and the CAD engine 28C manufactured by Company C.

Each of the CAD engine 28A manufactured by Company A, the CAD engine 28B manufactured by Company B, and the CAD engine 28C manufactured by Company C executes processing on the medical image for learning 30 and acquires a lung tumor labeling image as a temporary correct answer image 34. Specifically, the CAD engine 28A manufactured by Company A acquires a temporary correct answer image 34A, the CAD engine 28B manufactured by Company B acquires a temporary correct answer image 34B, and the CAD engine 28C manufactured by Company C acquires a temporary correct answer image 34C.

In FIG. 2, the temporary correct answer image 34A in which two lung tumors 35 are detected, the temporary correct answer image 34B in which three lung tumors 35 are detected, and the temporary correct answer image 34C in which one lung tumor 35 is detected are illustrated.

A set of the temporary correct answer image 34A, the temporary correct answer image 34B, and the temporary correct answer image 34C is input to a result-integrated CNN 18C. The result-integrated CNN 18C is trained to output the correct answer mask image 32 in a case in which a set of the temporary correct answer image 34A, the temporary correct answer image 34B, and the temporary correct answer image 34C is input.

In a case of the learning of the result-integrated CAD processing server 18, a set of the temporary correct answer image 34A, the temporary correct answer image 34B, and the temporary correct answer image 34C may be input to the result-integrated CNN 18C instead of the medical image for learning 30. The temporary correct answer image 34A, the temporary correct answer image 34B, and the temporary correct answer image 34C, which are described in the embodiment, are examples of first correct answer data, and are also examples of second correct answer data. For example, in a case in which the temporary correct answer image 34A is the first correct answer data, each of the temporary correct answer image 34B and the temporary correct answer image 34C is the second correct answer data. The term "data" includes the concepts of signals and information.

[Medical Image Diagnostic System Evaluation Method According to Embodiment]

The medical image diagnostic system 10 evaluates the characteristics of each of the plurality of CAD processing servers 16 based on the integrated discrimination result 26. In addition, the medical image diagnostic system 10 evaluates contribution of each of the plurality of CAD processing servers 16 to the integrated discrimination result 26 based on the integrated discrimination result 26 and the definitive diagnosis result by the doctor.

Examples of the characteristics of the CAD processing server 16 include a special site, a special lesion, and a special type of the medical image. As the special site, a region obtained by subdividing the site may be used. The type of the medical image can be grasped as a type of the modality that generates the medical image. The type of the medical image includes, for example, an MM image and a CT image.

The medical image diagnostic system 10 can evaluate the characteristics of the CAD processing server 16, and execute re-learning of the result-integrated CNN 18C based on an evaluation result. For example, in a case in which the CAD processing server 16A manufactured by Company A specializes in discriminating a right lung, in discrimination processing of the right lung, re-learning of the result-integrated CNN 18C can be executed in which the result-integrated CAD processing server 18 actively adopts the discrimination result 24A of the CAD processing server 16A manufactured by Company A. In other words, in a case of performing the discrimination processing of the right lung, the result-integrated CAD processing server 18 performs re-learning of the result-integrated CNN 18C by weighting the discrimination result of the CAD processing server 16 that specializes in discriminating the right lung. That is, the result-integrated CAD processing server 18 performs re-learning of the result-integrated CNN 18C by weighting, according to a site to be subjected to the discrimination processing, the discrimination result of the CAD processing server 16 that specializes in discriminating the site.

A degree of contribution representing the contribution of the CAD processing server 16 to the integrated discrimination result 26 can be said to be a necessity of each CAD processing server 16. The degree of contribution of the CAD processing server 16 can be derived based on the number of cases adopted in the integrated discrimination result 26 and the number of cases adopted in the definitive diagnosis result by the doctor.

Accordingly, the user of the medical image diagnostic system 10 can grasp the CAD processing server 16 having relatively low contribution to the improvement of the discrimination accuracy of the integrated discrimination result 26 based on the degree of contribution of each CAD processing server 16.

In addition, the user of the medical image diagnostic system 10 can execute billing stop, deletion from the lineup, and the like for the CAD processing server 16 having relatively low contribution. In addition, the user can prompt the company that manages the CAD processing server 16 to improve the CAD processing server 16, or the like.

That is, the medical image diagnostic system 10 executes the performance evaluation for all of the plurality of CAD processing servers 16, and calculates and stores the degree of contribution to the integrated discrimination result 26. The user of the medical image diagnostic system 10 can grasp the redundancy of the discrimination result 24 and the performance of the CAD processing server 16 as the number of times of repeated discrimination processing increases, and can narrow down the use to about one or two CAD processing servers 16 out of the plurality of CAD processing servers 16.

Figure 3:
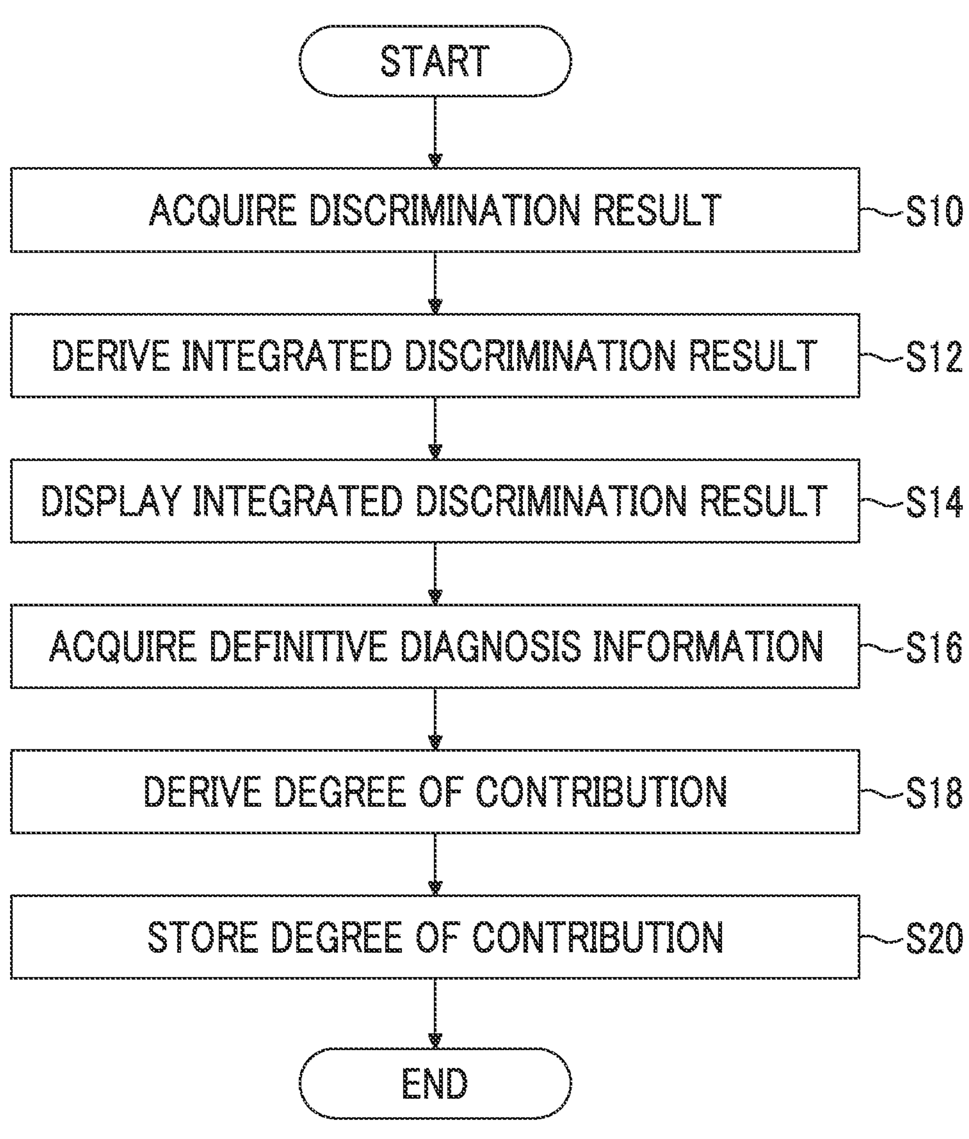
FIG. 3 is a flowchart showing a procedure of a medical image diagnostic system evaluation method according to the embodiment.

FIG. 3 is a flowchart showing a procedure of the medical image diagnostic system evaluation method according to the embodiment. In a discrimination result acquisition step S10, the result-integrated CAD processing server 18 shown in FIG. 1 acquires a set of the respective discrimination results 24 for one medical image from the plurality of CAD processing servers 16, and stores the acquired set of the discrimination results 24.

In an integrated discrimination result derivation step S12, the result-integrated CAD processing server 18 derives the integrated discrimination result 26 based on the set of the discrimination results 24 acquired in the discrimination result acquisition step S10, and stores the integrated discrimination result 26.

Specifically, in the integrated discrimination result derivation step S12, a set of the discrimination result 24A, the discrimination result 24B, and the discrimination result 24C is input to the trained result-integrated CNN 18C, and the integrated discrimination result 26 is output from the result-integrated CNN 18C.

In an integrated discrimination result display step S14, the result-integrated CAD processing server 18 displays the integrated discrimination result 26 on the display device 20B.

In a definitive diagnosis information acquisition step S16, the result-integrated CAD processing server 18 acquires the definitive diagnosis information including the definitive diagnosis by the doctor, which is input by using the input device 20A. The result-integrated CAD processing server 18 stores the acquired definitive diagnosis information in association with the integrated discrimination result 26.

In a degree-of-contribution derivation step S18, the degree of contribution of each CAD processing server 16 is derived based on the integrated discrimination result 26 and the definitive diagnosis information. As the degree of contribution of each CAD processing server 16, a score representing the contribution of the discrimination result 24 to the integrated discrimination result 26 can be used.

In a degree-of-contribution storage step S20, the result-integrated CAD processing server 18 stores the degree of contribution of each CAD processing server 16 derived in the degree-of-contribution derivation step S18.

The procedure shown in FIG. 3 may be executed in a case in which the integrated discrimination result 26 of the medical image 22 is newly acquired, or may be executed based on an input signal of the user. Each time the procedure shown in FIG. 3 is executed, the degree of contribution of each CAD processing server 16 may be updated.

[Detailed Description of Evaluation of CAD Processing Server]

FIG. 4 is a table showing an example of an evaluation result of the CAD processing server. FIG. 4 shows evaluation results of the CAD processing server 16A manufactured by Company A, the CAD processing server 16B manufactured by Company B, and the CAD processing server 16C manufactured by Company C, which are shown in FIG. 1. In the table shown in FIG. 4, the numerical value in the column labeled "Times" represents the number of times of the discrimination processing. The number of times of the discrimination processing shown in the table of FIG. 4 can be grasped as the identification number of the medical image to be processed.

In the table shown in FIG. 4, the term "detection" represents a case in which an abnormality candidate such as a lesion candidate is detected from the medical image 22. The term "non-detection" represents a case in which an abnormality candidate is not detected from the medical image 22. For example, the CAD processing server 16A manufactured by Company A and the CAD processing server 16C manufactured by Company C detect an abnormality candidate in all of the first processing to the fourth processing. On the other hand, the CAD processing server 16B manufactured by Company B detects an abnormality candidate in the second processing, but does not detect an abnormality candidate in the first processing, the third processing, and the fourth processing.

In the table shown in FIG. 4, the term "adoption" represents a case in which the discrimination result is adopted for the definitive diagnosis by the doctor. The term "non-adoption" represents a case in which the discrimination result is not adopted in the definitive diagnosis by the doctor. For example, in the CAD processing server 16A manufactured by Company A, the discrimination result is adopted for the definitive diagnosis by the doctor in all of the first processing to the fourth processing.

On the other hand, the CAD processing server 16B manufactured by Company B detects an abnormality candidate in the second processing, but the discrimination result is not adopted for the definitive diagnosis by the doctor, and the discrimination result of the CAD processing server 16A manufactured by Company A and the discrimination result of the CAD processing server 16C manufactured by Company C are adopted for the definitive diagnosis by the doctor.

On the other hand, the CAD processing server 16C manufactured by Company C detects an abnormality candidate in the first processing, but the discrimination result is not adopted for the definitive diagnosis by the doctor, and the discrimination result of the CAD processing server 16A manufactured by Company A is adopted for the definitive diagnosis by the doctor. In the CAD processing server 16C manufactured by Company C, the discrimination result is adopted for the definitive diagnosis by the doctor in the second processing to the fourth processing.

Based on the evaluation result of the CAD processing server shown in FIG. 4, the user can grasp that the CAD processing server 16A manufactured by Company A and the CAD processing server 16C manufactured by Company C have similar characteristics. Specifically, in the example shown in FIG. 4, the CAD processing server 16A manufactured by Company A and the CAD processing server 16C manufactured by Company C perform detection of an abnormality candidate for the same medical image 22. That is, it can be grasped that the servers that similarly detect the abnormality candidates for the same medical image 22 have similar characteristics. In addition, the CAD processing server 16A manufactured by Company A has a larger number of times of the discrimination result adopted for the definitive diagnosis by the doctor than the CAD processing server 16C manufactured by Company C. That is, the greater the number of times of the discrimination result adopted for the definitive diagnosis by the doctor, the higher the degree of contribution, and the smaller the number of times, the lower the degree of contribution. Accordingly, the user can consider stopping the use of the CAD processing server 16C manufactured by Company C having a relatively low degree of contribution out of the CAD processing server 16A manufactured by Company A and the CAD processing server 16C manufactured by Company C, which have similar characteristics. In addition, the user can consider stopping the use of the CAD processing server 16B manufactured by Company B having the lowest degree of contribution.

The result-integrated CAD processing server 18 may calculate a score representing the degree of contribution of each CAD processing server 16 based on the evaluation result of the CAD processing server 16 shown in FIG. 4. In other words, the result-integrated CAD processing server 18 may calculate a score representing the degree of contribution based on the detection characteristic (performance) of the abnormality candidate and the adoption result of the definitive diagnosis. Specifically, a high score may be assigned in a case in which an abnormality candidate is detected and is adopted for the definitive diagnosis, a medium score may be assigned in a case in which an abnormality candidate is detected and is not adopted for the definitive diagnosis, and a low score may be assigned in a case in which an abnormality candidate is not detected. For example, +1 point is given in a case in which an abnormality candidate is detected and is adopted for the definitive diagnosis by the doctor, −0.5 points are given in a case in which an abnormality candidate is detected and is not adopted for the definitive diagnosis by the doctor, and −2 points are given in a case in which an abnormality candidate is not detected. The result-integrated CAD processing server 18 can calculate an overall evaluation score of each CAD processing server 16 obtained by summing up the scores.

In addition, the result-integrated CAD processing server 18 may issue a warning in a case in which a ratio of the number of times of the detection of the abnormality candidate to the number of times of the discrimination processing is equal to or less than a prescribed value, or may issue a warning in a case in which a ratio of the number of times of the adoption to the number of times of the discrimination processing is equal to or less than a prescribed value.

The score of each CAD processing server 16 described in the embodiment is an example of a first score and an example of a second score. In other words, the score of each of the CAD processing servers 16A, 16B, and 16C is a first score or a second score.

FIG. 5 is a schematic diagram showing a configuration example of an evaluation result of the CAD processing server. FIG. 5 shows an evaluation result of the CAD processing server 16 derived for each site. Specifically, FIG. 5 shows an evaluation result of the CAD processing server 16 derived for a lung, an evaluation result of the CAD processing server 16 derived for a heart, and an evaluation result of the CAD processing server 16 derived for a bronchus. The result-integrated CAD processing server 18 executes the evaluation of the CAD processing server 16 for each site, and derives an evaluation result of the CAD processing server 16 for each site. The medical image diagnostic system 10 can derive a degree of contribution of each CAD processing server 16 for each site. In addition, the medical image diagnostic system 10 can perform the performance evaluation for the CAD processing server 16 with respect to a site such as a special site, based on the evaluation result of the CAD processing server 16 for each site.

FIG. 6 is a schematic diagram showing another configuration example of an evaluation result of the CAD processing server. FIG. 6 shows an evaluation result of the CAD processing server 16 derived for each region obtained by subdividing a site. In FIG. 6, a right lung, a left lung, a lung segment S1, and a lung segment S2 are illustrated as an example of the region.

For example, in regard to a pulmonary nodule, the CAD processing server 16 may be evaluated separately according to the nature and occurrence location of the pulmonary nodule, and whether or not to use the CAD processing server 16 according to the nature and occurrence location of the pulmonary nodule may be optimized. In other words, a configuration may be used in which the plurality of CAD processing servers 16A, 16B, and 16C are evaluated for each region corresponding to the type or occurrence location of a lesion, and suitable CAD processing servers 16A, 16B, and 16C can be used according to the type or occurrence location of the lesion.

[Configuration Example of Display Screen]

Figure 7:
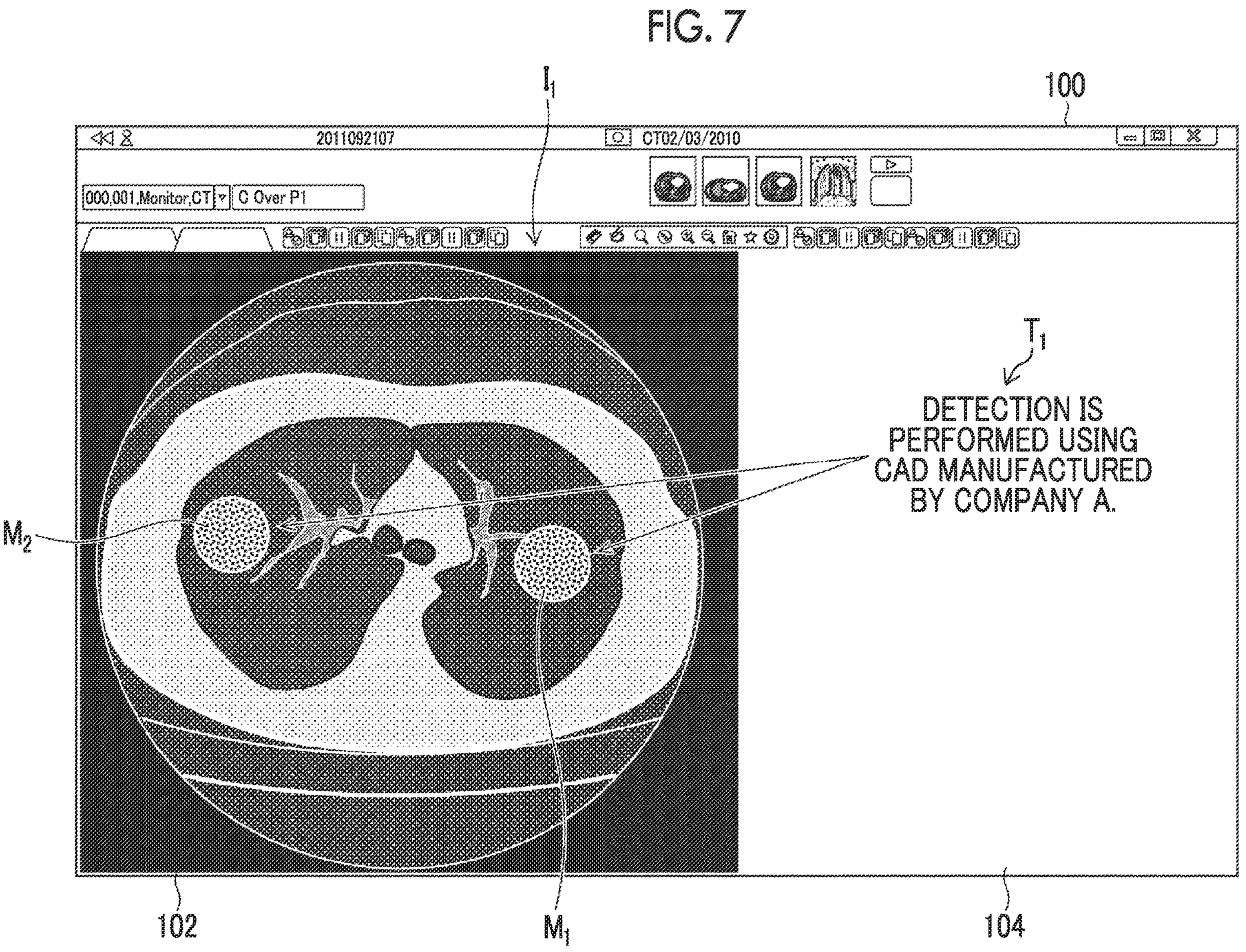
FIG. 7 is a diagram showing an example of a discrimination result screen.

FIG. 7 is a diagram showing an example of a discrimination result screen. A discrimination result screen 100 shown in FIG. 7 is one aspect of notifying of the integrated discrimination result 26 shown in FIG. 1, and is displayed using the display device 20B shown in FIG. 1. In the discrimination result screen 100, a CT image $I_1$ is displayed in a first region 102, and a marker $M_1$ and a marker $M_2$ surrounding a lesion region detected from the CT image $I_1$ are superimposed and displayed on the CT image In the discrimination result screen 100, an explanatory text $T_1$ for the CT image $I_1$ and for the lesion region surrounded by the marker $M_1$ is displayed in a second region 104 disposed on the right side of the CT image $I_1$. In FIG. 7, as the explanatory text $T_1$ for the CT image $I_1$, character information representing that the detection is performed using the CAD processing server 16A manufactured by Company A is displayed.

Figure 8:
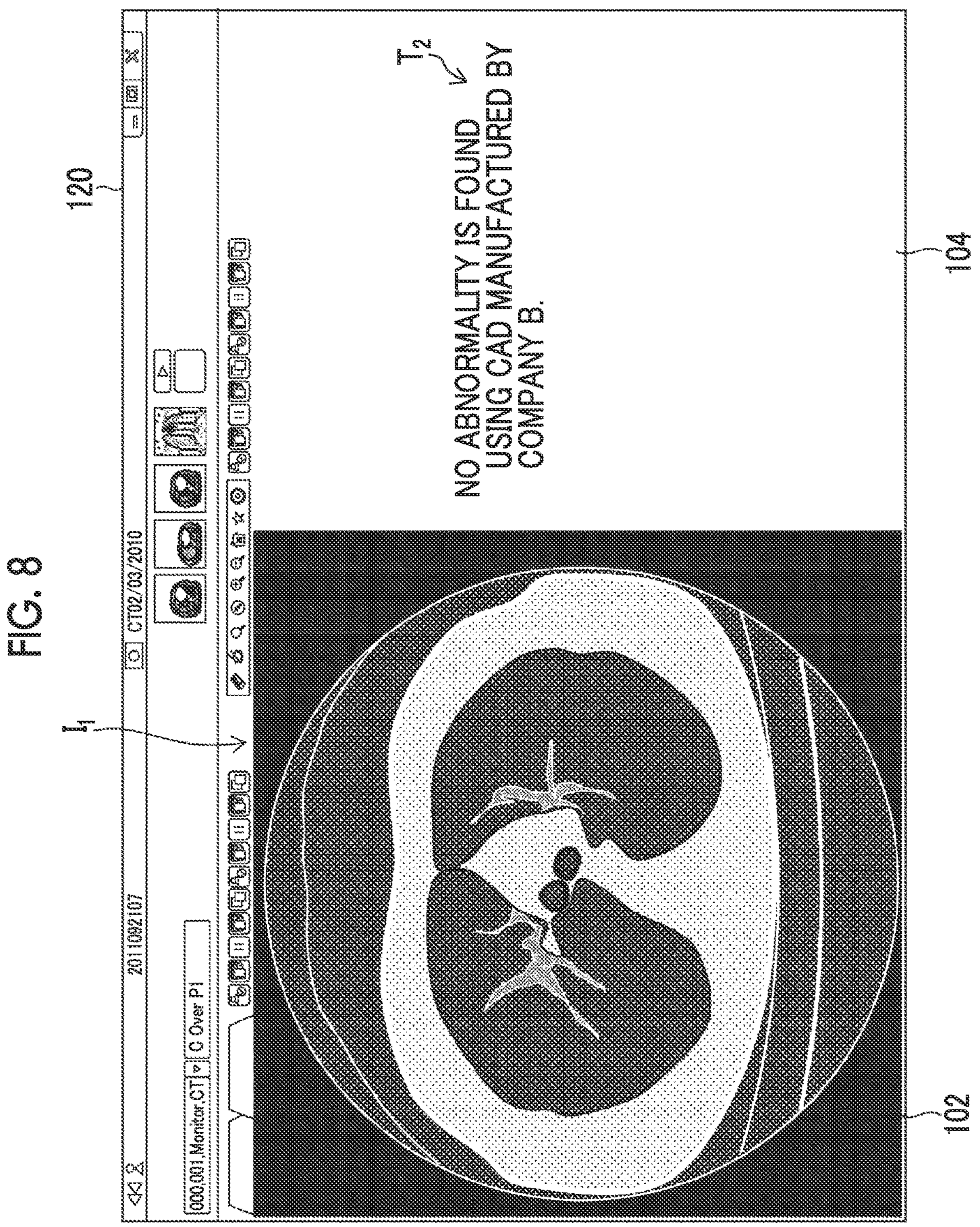
FIG. 8 is a diagram showing another example of a discrimination result screen.

FIG. 8 is a diagram showing another example of a discrimination result screen. A discrimination result screen 120 shown in FIG. 8 is displayed using the display device 20B shown in FIG. 1. The discrimination result screen 120 is used in a case in which no lesion region is detected from the CT image $I_1$.

In the discrimination result screen 120, the CT image $I_1$ is displayed in the first region 102. On the other hand, the marker $M_1$, the marker $M_2$, and the like shown in FIG. 7 are not displayed in the discrimination result screen 120.

In the discrimination result screen 120, an explanatory text $T_2$ for the CT image $I_1$ is displayed in the second region 104. In FIG. 8, as the explanatory text $T_2$ for the CT image $I_1$, character information representing that no abnormality is detected using the CAD processing server 16B manufactured by Company B is displayed. The explanatory text $T_2$ shown in FIG. 8 may be displayed together with the explanatory text $T_1$ shown in FIG. 7.

As shown in FIGS. 7 and 8, the result-integrated CAD processing server 18 can notify of the discrimination results 24 of the plurality of CAD processing servers 16 shown in FIG. 1 on a discrimination result display screen for displaying the integrated discrimination result 26.

The result-integrated CAD processing server 18 may selectively switch between display and non-display of the explanatory text $T_1$ or the like for the CT image $I_1$. For example, display and non-display of the explanatory text $T_1$ or the like may be selectively switched according to selection information input by the user by using the input device 20A shown in FIG. 1.

Effects of Embodiment

The medical image diagnostic system, the medical image diagnostic system evaluation method, and the program according to the embodiment can obtain the following effects.

[1]

In the medical image diagnostic system 10 that derives the integrated discrimination result 26 based on the discrimination results 24 of the plurality of CAD processing servers 16 for the same site and the same lesion, the degree of contribution representing the contribution of the discrimination result 24 to the integrated discrimination result 26 is derived. With this, it is possible to grasp the CAD processing server 16 with relatively low contribution to improvement in the accuracy of the integrated discrimination result 26.

[2]

The degree of contribution representing the contribution of the discrimination result 24 to the integrated discrimination result 26 is derived for each site and for each region obtained by subdividing the site. With this, it is possible to grasp the specialty and non-specialty of each CAD processing server 16 with respect to the site and the region. In addition, it is possible to grasp the necessity of the CAD processing server 16 for each site and region.

[3]

The degree of contribution representing the contribution of the discrimination result 24 to the integrated discrimination result 26 is derived based on the adoption and non-adoption for the definitive diagnosis by the doctor. With this, it is possible to evaluate the CAD processing server 16 based on the definitive diagnosis by the doctor.

[Modification Example of Medical Image Diagnostic System]

The components constituting the medical image diagnostic system shown in FIG. 1 can be integrated and separated as appropriate. For example, the result-integrated CAD processing server 18 and the like may be configured by using a plurality of computers.

For example, a part or the whole of the image storage server 14 and a part or the whole of the result-integrated CAD processing server 18 may be configured by using one computer.

The technical scope of the present invention is not limited to the scope described in the above embodiments. The configurations and the like in each embodiment can be appropriately combined between the respective embodiments without departing from the spirit of the present invention.

EXPLANATION OF REFERENCES

10: medical image diagnostic system
12: modality
14: image storage server
16: CAD processing server
16A: CAD processing server manufactured by Company A
16B: CAD processing server manufactured by Company B
16C: CAD processing server manufactured by Company C
18: result-integrated CAD processing server
18A: processor
18B: memory
20: PACS viewer
20A: input device
20B: display device
22: medical image
24: discrimination result
24A: discrimination result
24B: discrimination result
24C: discrimination result 26: integrated discrimination result
28A: CAD engine manufactured by Company A
28B: CAD engine manufactured by Company B
28C: CAD engine manufactured by Company C
29: CAD result
30: medical image for learning
32: correct answer mask image
34: temporary correct answer image
34A: temporary correct answer image
34B: temporary correct answer image
34C: temporary correct answer image
35: lung tumor
100: screen
102: first region
104: second region
120: screen
$I_1$: CT image
$M_1$: marker
$M_2$: marker
$T_1$: explanatory text
$T_2$: explanatory text
S10 to S20: each step of medical image diagnosis

What is claimed is:

1. A medical image diagnostic system comprising:
a processor; and
a memory that stores one or more commands executed by the processor,
wherein the processor
acquires a first discrimination result from a first discrimination device that executes first discrimination intended for a predetermined site and a predetermined lesion, on a medical image,
acquires a second discrimination result from a second discrimination device that executes second discrimination intended for the predetermined site and the predetermined lesion, which are the same as those for which the discrimination of the first discrimination device is intended, on the medical image,
derives an integrated discrimination result in which the first discrimination result and the second discrimination result are integrated, by using an integrated discrimination device, which is a trained learning model that has trained using a set of the medical image and a correct answer image in which a lesion is detected from the medical image, as learning data, and
derives a degree of contribution of the first discrimination device to the integrated discrimination result and a degree of contribution of the second discrimination device to the integrated discrimination result based on the integrated discrimination result and a definitive diagnosis result by a doctor,
wherein the integrated discrimination device uses the trained learning model that has trained using a set of the correct answer image, first correct answer data output from the first discrimination device in a case in which the medical image is input to the first discrimination device, and second correct answer data output from the second discrimination device in a case in which the medical image is input to the second discrimination device, as learning data.

2. The medical image diagnostic system according to claim 1,
wherein the processor
derives a first score representing the degree of contribution of the first discrimination device to the integrated discrimination result, and
derives a second score representing the degree of contribution of the second discrimination device to the integrated discrimination result.

3. The medical image diagnostic system according to claim 1,
wherein the processor evaluates the contribution of the first discrimination device and the second discrimination device to the integrated discrimination result, for each predetermined site.

4. The medical image diagnostic system according to claim 1,
wherein the processor evaluates the contribution of the first discrimination device and the second discrimination device to the integrated discrimination result, for each region obtained by subdividing the predetermined site.

5. The medical image diagnostic system according to claim 1,
wherein the processor causes a display device to display at least one of the first discrimination result or the second discrimination result.

6. The medical image diagnostic system according to claim 1,
wherein the processor acquires input information representing the definitive diagnosis result by the doctor, which is input by using an input device.

7. The medical image diagnostic system according to claim 1, further comprising:
an image storage device that stores the medical image,
wherein the processor acquires the medical image from the image storage device.

8. The medical image diagnostic system according to claim 1,
wherein the medical image diagnostic system includes the first discrimination device and the second discrimination device.

9. A medical image diagnostic system evaluation method executed by a computer, the method comprising:
acquiring a first discrimination result obtained by executing first discrimination intended for a predetermined site and a predetermined lesion, on a medical image;
acquiring a second discrimination result obtained by executing second discrimination intended for the predetermined site and the predetermined lesion, which are the same as those for which the first discrimination is intended, on the medical image;
deriving an integrated discrimination result in which the first discrimination result and the second discrimination result are integrated, by using an integrated discrimination device, which is a trained learning model that has trained using a set of the medical image and a correct answer image in which a lesion is detected from the medical image, as learning data; and
deriving a degree of contribution of the first discrimination to the integrated discrimination result and a degree of contribution of the second discrimination to the integrated discrimination result based on the integrated discrimination result and a definitive diagnosis result by a doctor,
wherein the integrated discrimination device uses the trained learning model that has trained using a set of the correct answer image, first correct answer data output from the first discrimination device in a case in which the medical image is input to the first discrimination device, and second correct answer data output from the second discrimination device in a case in which the medical image is input to the second discrimination device, as learning data.

10. A non-transitory, computer-readable tangible recording which records thereon a program for causing, when read by a computer, the computer to execute:

acquiring a first discrimination result obtained by executing first discrimination intended for a predetermined site and a predetermined lesion, on a medical image;

acquiring a second discrimination result obtained by executing second discrimination intended for the predetermined site and the predetermined lesion, which are the same as those for which the first discrimination is intended, on the medical image;

deriving an integrated discrimination result in which the first discrimination result and the second discrimination result are integrated, by using an integrated discrimination device, which is a trained learning model that has trained using a set of the medical image and a correct answer image in which a lesion is detected from the medical image, as learning data; and deriving a degree of contribution of the first discrimination to the integrated discrimination result and a degree of contribution of the second discrimination to the integrated discrimination result based on the integrated discrimination result and a definitive diagnosis result by a doctor, wherein the integrated discrimination device uses the trained learning model that has trained using a set of the correct answer image, first correct answer data output from the first discrimination device in a case in which the medical image is input to the first discrimination device, and second correct answer data output from the second discrimination device in a case in which the medical image is input to the second discrimination device, as learning data.

* * * * *